United States Patent
Ito et al.

(10) Patent No.: US 7,615,332 B2
(45) Date of Patent: Nov. 10, 2009

(54) PHOTOSENSITIVE COMPOUND, PHOTOSENSITIVE COMPOSITION, RESIST PATTERN FORMING METHOD, AND DEVICE PRODUCTION PROCESS

(75) Inventors: Toshiki Ito, Kawasaki (JP); Takako Yamaguchi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/021,250

(22) Filed: Jan. 28, 2008

(65) Prior Publication Data

US 2008/0187864 A1    Aug. 7, 2008

(30) Foreign Application Priority Data

Feb. 6, 2007    (JP)    ............................. 2007-027367
Oct. 31, 2007    (JP)    ............................. 2007-284378

(51) Int. Cl.
*G03F 7/039*    (2006.01)
*G03F 7/20*    (2006.01)
*G03F 7/30*    (2006.01)
*G03F 7/36*    (2006.01)
*G03F 7/40*    (2006.01)

(52) U.S. Cl. .................... 430/270.1; 430/905; 430/907; 430/325; 430/326; 430/311; 430/312; 430/313; 430/314; 430/316; 549/283; 549/288; 549/289; 549/290; 549/399; 525/386; 525/480; 525/333.3

(58) Field of Classification Search ........................ None
See application file for complete search history.

(56) References Cited

U.S. PATENT DOCUMENTS

| | | | |
|---|---|---|---|
| 4,859,563 | A | 8/1989 | Miura et al. |
| 6,849,391 | B2 | 2/2005 | Yamaguchi et al. .......... 430/326 |
| 7,022,463 | B2 | 4/2006 | Yamaguchi et al. .......... 430/291 |
| 2005/0084793 | A1 | 4/2005 | Yueh et al. |
| 2005/0221222 | A1 | 10/2005 | Ito et al. .................... 430/270.1 |
| 2006/0003269 | A1 | 1/2006 | Ito et al. ..................... 430/323 |
| 2006/0014108 | A1 | 1/2006 | Ito et al. ..................... 430/322 |
| 2007/0141483 | A1 | 6/2007 | Yamaguchi et al. |
| 2007/0218373 | A1 | 9/2007 | Ito et al. |
| 2007/0218398 | A1 | 9/2007 | Ito et al. |
| 2007/0287105 | A1 | 12/2007 | Ito et al. ..................... 430/346 |
| 2008/0085479 | A1 | 4/2008 | Yamaguchi et al. |
| 2008/0187865 | A1 | 8/2008 | Ito et al. |

OTHER PUBLICATIONS

Lu et al ("Synthesis of Coumarin-functionalized Calix[4]arene and Selective Recognition for L-Tryptophan", Chinese Chemical Letters, vol. 17, No. 5, pp. 575-577 (2006)).*
U.S. Appl. No. 10/585,644, International Filing date Jul. 7, 2006, Inventor(s) Toshiki Ito, et al.
Database CA [Online], Chemical Abstracts Service, Columbus, Ohio, US; Yun Jung Jang, et al., "New cavitand derivatives bearing four coumarin groups as fluorescent chemosensors for Cu2+ and recognition of dicarboxylates utilizing Cu2+ complex" Tetrahedron Letters 47 (2006) pp. 2707-2710 XP002482870.
Database CA [Online], Chemical Abstracts Service, Columbus, Ohio, US; De-Hua Zhang, et al., "Synthesis of difunctional calix[4]arene containing coumarin and crown ether" XP002482871 (2006).
Jian Quan Lu, et al., "Synthesis of coumarin-functionalized calix[4]arene and selective recognition for L-tryptophan" XP002482872 (2006).
Search Report Dated Jul. 16, 2008; in European Application No. EP 08151053.9.
Hirayama, et al., "New Photoresist-Based on Amorphous Low Molecular Weight Polyphenols", Journal of Photopolymer Science and Technology, vol. 17, No. 3, 2004, pp. 435-440.
Honda, et al., "What determines the ultimate resolution? The critical relationship between exposure tools and photoresists", Proc. of SPIE, vol. 6154, 2006, pp. 615422-1-615422-9.
Official Action dated Jun. 22, 2009 in Korean Application No. 10-2008-0011497.
Jang, et al., "New cavitand derivatives bearing four coumarin groups as fluorescent chemosensors for Cu2+ and recognition of dicarboxylates utilizing Cu2+ complex", Tetrahedron Letters, vol. 47, 2006, pp. 2707-2710.

* cited by examiner

*Primary Examiner*—Sin J. Lee
(74) *Attorney, Agent, or Firm*—Fitzpatrick, Cella, Harper & Scinto

(57) ABSTRACT

A photosensitive compound has two or more structural units, in a molecule, represented by the following general formula (1):

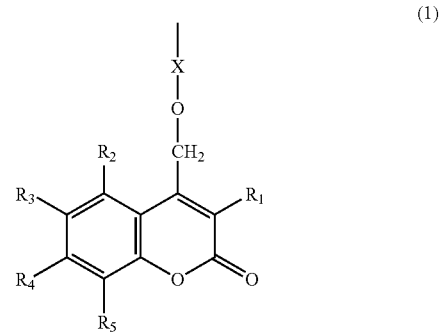

wherein $R_1$ to $R_5$ are selected from the group consisting of hydrogen atom, halogen atom, alkyl group, alkoxy group, acetoxy group, phenyl group, naphthyl group, and alkyl group in which a part or all of hydrogen atoms are substituted with fluorine atom; and X is a substituted or unsubstituted phenylene group or a substituted or unsubstituted naphthylene group.

13 Claims, 2 Drawing Sheets

PHOTOSENSITIVE COMPOUND, PHOTOSENSITIVE COMPOSITION, RESIST PATTERN FORMING METHOD, AND DEVICE PRODUCTION PROCESS

FIELD OF THE INVENTION AND RELATED ART

The present invention relates to a photosensitive compound, a photosensitive composition containing the photosensitive compound dissolved in a solvent, a resist pattern forming method using the photosensitive composition, and a process for producing a device by using the resist pattern forming method.

In recent years, demands for high density and high integration of devices have been increasing more and more in the fields of various electronic devices, requiring fine processing, including a semiconductor device. In a semiconductor device production process, a photolithographic process (photolithography) plays an important role in forming a fine pattern. In the photolithography, a technique capable of stably performing fine processing with an accuracy of 100 nm or less is required. For this reason, a resist used is also required so that a pattern of 100 nm or less can be formed with accuracy.

As a conventional popular resist, diazonaphthoquinone-novolak type resists based on a dissolution inhibition effect of a diazonaphthoquinone compound on a phenolic resin material have been known (U.S. Pat. No. 4,859,563).

When a low-molecular weight phenolic resin material is used in the diazonaphthoquinone-novolak type resists, the dissolution inhibition effect of the diazonaphthoquinone compound is not sufficiently achieved, so that a development contrast between an exposed portion and an unexposed portion is low.

Lately, as a resist capable of providing a higher resolution than the diazonaphthoquinone-novolak type resist, a chemically amplified resist has been used. The chemically amplified resist generates an acid ($H^+$) by active ray irradiation and causes deprotection reaction of an alkali-soluble group protected with an acid-degradable group, thus being solubilized in alkali (Journal of Photopolymer Science and Technology, 17, 435 (2004)).

When a resist pattern of the chemically amplified resist is prepared, heat treatment is performed before development in order to accelerate the deprotection reaction in the presence of the acid, as a catalyst, generated at the exposed portion.

During the heat treatment, the acid is diffused by heat in a length of approximately 10 nm ("Proc. SPIE", 6154, 710 (2006)). As a result, line edge roughness (LER) which is minute projections and recesses at an edge portion of the resist pattern is caused to occur and the acid diffusion leads to a lowering in resolution.

Another factor causing the LER may include an influence of a molecular weight of a base compound. Herein, the base compound means a compound having an alkali-soluble group or a protected alkali-soluble group in a resist composition.

Dissolution of the base compound in a developing liquid is caused to occur at one molecule unit of the base compound, so that the LER is larger with a large molecule weight.

A lower-molecule weight compound has a lower glass transition temperature and a lower melting point. The chemically amplified resist has a long acid diffusion length when the heat treatment before development is performed at a temperature higher than a glass transition temperature thereof, so that a resultant resolution is lowered.

In other words, the base compound for the chemically amplified resist is required to have a glass transition temperature higher than a deprotection reaction temperature in the presence of the acid catalyst. This requirement constitutes a constraint on a lower LER design, i.e., a lower-molecule weight design of the chemically amplified resist.

According to a study by the present inventors, it was confirmed that the chemically amplified resist further increases the LER of the resist pattern when the resist was diluted with an organic solvent, applied in a thickness of about 10 nm, and used in pattern formation using near-field light exposure.

In place of the chemically amplified resist, a new photosensitive material capable of providing a low LER is required.

SUMMARY OF THE INVENTION

A principal object of the present invention is to provide a photosensitive compound capable of forming a resist pattern with a low LER (line edge roughness).

Another object of the present invention is to provide a photosensitive composition in which the photosensitive compound is dissolved in a solvent, a resist pattern forming method using the photosensitive composition, and a device production process using the resist pattern.

According to a first aspect of the present invention, there is provided a photosensitive compound comprising:

two or more structural units, in a molecule, represented by the following general formula (1):

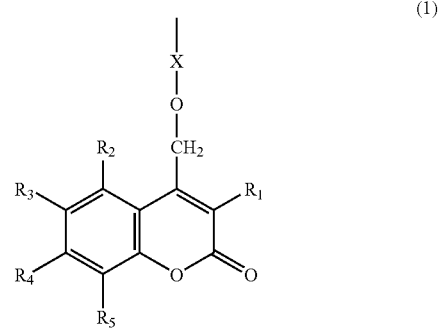

wherein $R_1$ to $R_5$ are selected from the group consisting of hydrogen atom, halogen atom, alkyl group, alkoxy group, acetoxy group, phenyl group, naphthyl group, and alkyl group in which a part or all of hydrogen atoms are substituted with fluorine atom; and X is a substituted or unsubstituted phenylene group or a substituted or unsubstituted naphthylene group.

According to a second aspect of the present invention, there is provided a photosensitive compound comprising:

two or more structural units, in a molecule, represented by the following general formula (2):

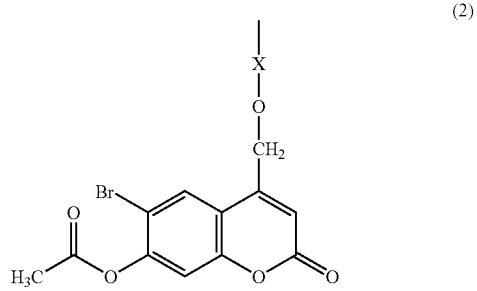

wherein X is a substituted or unsubstituted phenylene group or a substituted or unsubstituted naphthylene group.

According to a third aspect of the present invention, there is provided a photosensitive compound comprising:

two or more structural units, in a molecule, represented by the following general formula (3):

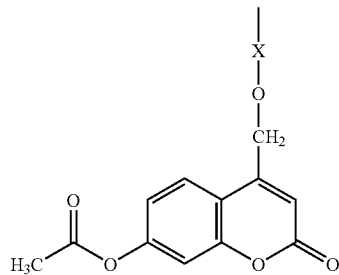

(3)

wherein X is a substituted or unsubstituted phenylene group or a substituted or unsubstituted naphthylene group.

According to a fourth aspect of the present invention, there is provided a photosensitive compound comprising:

two or more structural units, in a molecule, represented by the following general formula (4):

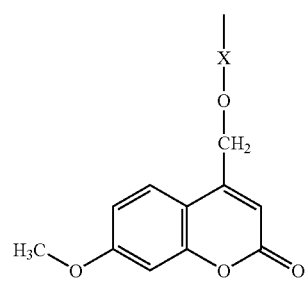

(4)

wherein X is a substituted or unsubstituted phenylene group or a substituted or unsubstituted naphthylene group.

According to a fifth aspect of the present invention, there is provided a photosensitive compound comprising:

two or more structural units, in a molecule, represented by the following general formula (5):

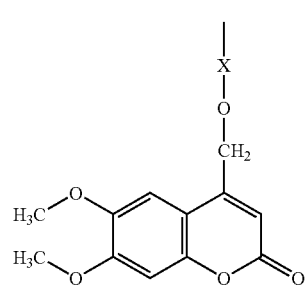

(5)

wherein X is a substituted or unsubstituted phenylene group or a substituted or unsubstituted naphthylene group.

According to a sixth aspect of the present invention, there is provided a photosensitive compound comprising:

two or more structural units, in a molecule, represented by the following general formula (6):

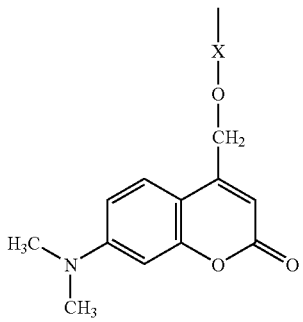

(6)

wherein X is a substituted or unsubstituted phenylene group or a substituted or unsubstituted naphthylene group.

According to a seventh aspect of the present invention, there is provided, as a photosensitive compound, polyhydroxystyrene comprising:

hydrogen atoms of two or more phenolic hydroxyl groups substituted with a substituent represented by the following general formula (7):

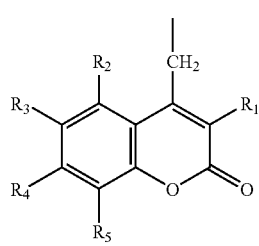

(7)

wherein $R_1$ to $R_{10}$ are selected from the group consisting of hydrogen atom, halogen atom, alkyl group, alkoxy group, acetoxy group, phenyl group, naphthyl group, and alkyl group in which a part or all of hydrogen atoms are substituted with fluorine atom.

According to a eighth aspect of the present invention, there is provided, as a photosensitive compound, carixarene comprising:

hydrogen atoms of two or more phenolic hydroxyl groups substituted with a substituent represented by the following general formula (7):

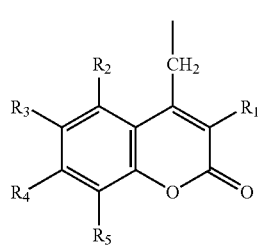

(7)

wherein $R_1$ to $R_{10}$ are selected from the group consisting of hydrogen atom, halogen atom, alkyl group, alkoxy group, acetoxy group, phenyl group, naphthyl group, and alkyl group in which a part or all of hydrogen atoms are substituted with fluorine atom.

According to a ninth aspect of the present invention, there is provided, as a photosensitive compound, novolak resin comprising:

hydrogen atoms of two or more phenolic hydroxyl groups substituted with a substituent represented by the following general formula (7):

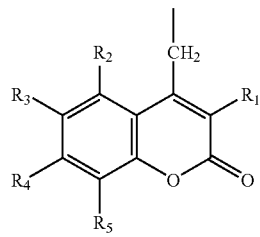

(7)

wherein $R_1$ to $R_{10}$ are selected from the group consisting of hydrogen atom, halogen atom, alkyl group, alkoxy group, acetoxy group, phenyl group, naphthyl group, and alkyl group in which a part or all of hydrogen atoms are substituted with fluorine atom.

The present invention includes a photosensitive composition, a resist pattern forming method, and a device production method.

The photosensitive composition of the present invention is characterized in that the photosensitive compound of the present invention is dissolved in an organic solvent.

The resist pattern forming method of the present invention is characterized by comprising a step of forming a photosensitive resist layer by applying the above-described photosensitive composition onto a substrate; a step of selectively irradiating the resist layer with radiation; and a step of forming a pattern of the resist layer by developing an irradiated portion of the resist layer.

The device production process of the present invention is characterized in that a device is formed on a substrate by using the resist pattern forming method of the present invention.

According to the present invention, it is possible to provide a photosensitive compound capable of forming a resist pattern with a low LER, a photosensitive composition in which the photosensitive compound is dissolved in an organic solvent, a resist pattern forming method using the photosensitive composition, and a device production process using the resist pattern.

These and other objects, features and advantages of the present invention will become more apparent upon a consideration of the following description of the preferred embodiments of the present invention taken in conjunction with the accompanying drawings.

DETAILED DESCRIPTION OF THE PREFERRED EMBODIMENTS

Figure 1:
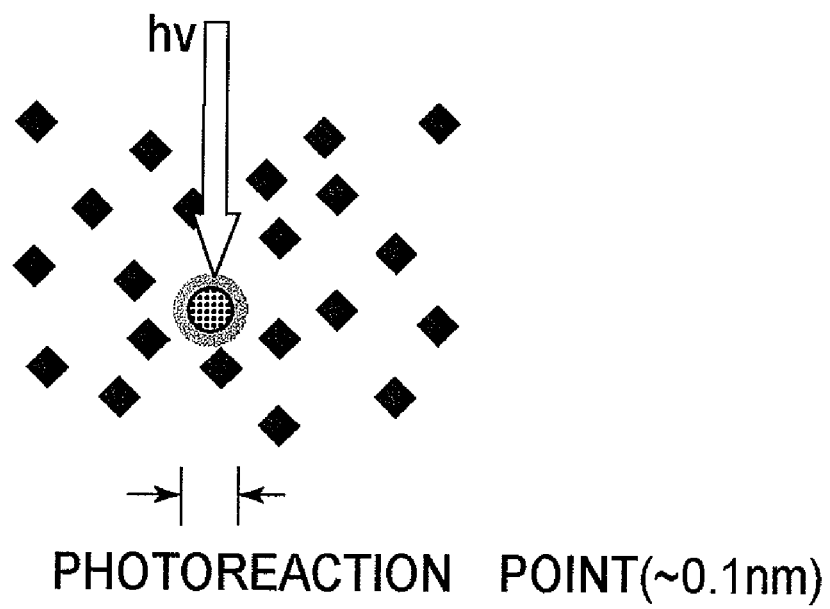
FIG. 1 is a schematic view for illustrating a photochemical reaction of a photosensitive composition according to the present invention.

Hereinbelow, the present invention will be described in detail.

In the present invention, the LER is defined as 3σ wherein σ represents a standard deviation of a line pattern width.

The thus defined LER is calculated from measured values of line pattern widths as a population. More specifically, in a line pattern including lines with lengths from 0.5 μm to 2 μm, sampling is made at 50 points or more at regular intervals of 10 nm with respect to a line length direction and a line pattern width is measured at each of the points. From the measured values of the line pattern widths, the LER is calculated. For the measurement of the line pattern widths, it is possible to use a scanning electron microscope, an atomic force microscope, or the like.

The photosensitive compound of the present invention comprises two or more structural units, in a molecule, represented by the following general formula (1):

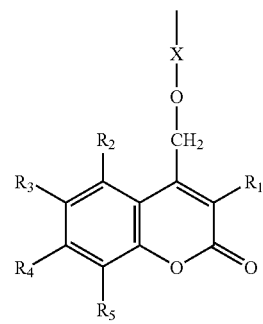

(1)

wherein $R_1$ to $R_5$ are selected from the group consisting of hydrogen atom, halogen atom, alkyl group, alkoxy group, acetoxy group, phenyl group, naphthyl group, and alkyl group in which a part or all of hydrogen atoms are substituted with fluorine atom; and X is a substituted or unsubstituted phenylene group or a substituted or unsubstituted naphthylene group.

The photosensitive compound comprising two or more structural units, in a molecule, represented by the above-described general formula (1) can be synthesized through a known condensation reaction between a coumarin (cumarin) derivative represented by a general formula (21) shown below and a polyhydric phenolic compound having two or more phenolic hydroxyl groups in a molecule (hereinafter referred to as a "polyphenolic compound"). By this condensation reaction, a phenolic hydroxyl group is coumarinyl-methyl-etherified to provide the structural units represented by the above-described general formula (21).

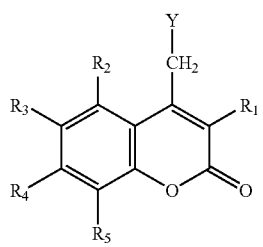

(21)

In the general formula (21), $R_1$ to $R_5$ have the same meanings as those defined above, and Y is hydroxyl group or a hydrogen atom.

Examples of the coumarin derivative represented by the general formula (21) may include: 4-(bromomethyl)umbelliferonyl acetate; 4-bromomethyl-6,7-dimethoxycoumarin; 4-bromomethyl-7-methoxycoumarin; and 4-chloromethyl-6-methylcoumarin.

Further, it is also possible to synthesis the coumarin derivative represented by the general formula (4) by halogenating 4-position methyl group of a 4-methylcoumarin derivative through a known method. Examples of the 4-methylcoumarin derivative may include: 7-dimethylamino-4-methylcoumarin; 7-diethylamino-4-methylcoumarin; 4,6-dimethylcoumarin; 7-ethoxy-4-methylcoumarin; 6-ethyl-7-methoxy-4-methylcoumarin; and 5,7-dimethoxy-4-methylcoumarin.

In the present invention, the polyphenolic compound can be classified into a polymeric compound and a low-molecule weight compound. In the present invention, it is preferable that a polymeric compound having a molecular weight dispersion of 1.0-1.5 or a low-molecular weight compound having a molecular weight dispersion of 1.0-1.5 is used. In the present invention, the low-molecular weight compound means a compound having a molecular weight of 2000 or less or a compound which is not a polymer obtained from one or more species of monomers.

The photosensitive compound of the present invention does not require heating after light exposure. For this reason, even a low-molecular weight compound which cannot be used for the chemically amplified resist due to the chemically amplified to the glass transition temperature and the melting point can be used in the present invention, so that a resist pattern with a low LER is formed by using the photosensitive compound of the present invention.

Examples of the polymeric polyphenolic compound in the present invention may include condensation reaction products between phenols and aldehydes, condensation reaction products between phenols and ketones, vinylphenol polymers such as polyhydroxystyrene, and isopropenylphenol polymers.

The polymeric polyphenolic may have a weight-average molecular weight of 1,000 or more and 100,000 or less, preferably 3,000 or more and 50,000 or less and a molecular weight dispersion of 1.0 or more and 3.0 or less, preferably 1.0 or more and 1.2 or less.

Particularly, a polyhydroxystyrene homopolymer having a weight-average molecular weight of 3,000 or more and 50,000 or less and a molecular weight dispersion of 1.0 or more and 1.2 or less is preferred. This is because a smaller molecular weight dispersion provides a smaller LER.

Examples of the condensation reaction products between the phenols and the aldehydes may include phenol-novolak resin, cresol-novolak resin, carixarene, and the like.

The thus obtained novolak resins, carixarene, and the like are embraced in the photosensitive compound of the present invention.

Carixarene as the photosensitive compound of the present invention comprises hydrogen atoms of two or more phenolic hydroxyl groups substituted with a substituent represented by the following general formula (7):

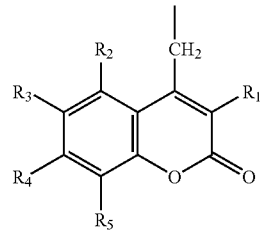

wherein $R_1$ to $R_{10}$ are selected from the group consisting of hydrogen atom, halogen atom, alkyl group, alkoxy group, acetoxy group, phenyl group, naphthyl group, and alkyl group in which a part or all of hydrogen atoms are substituted with fluorine atom.

Novolak resin as the photosensitive compound of the present invention comprises hydrogen atoms of two or more phenolic hydroxyl groups substituted with a substituent represented by the following general formula (7):

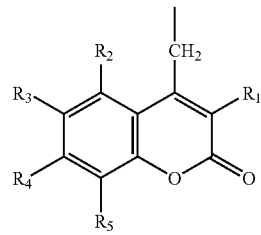

wherein $R_1$ to $R_{10}$ are selected from the group consisting of hydrogen atom, halogen atom, alkyl group, alkoxy group, acetoxy group, phenyl group, naphthyl group, and alkyl group in which a part or all of hydrogen atoms are substituted with fluorine atom.

Examples of the phenols used in synthesis of the condensation reaction product between the phenols and the aldehydes may include: monohydric phenols such as phenol, cresol, xylenol, ethylphenol, propylphenol, butylphenol, and phenylphenol; and polyhydric phenols such as resokinol, pyrocatecol, hydroquinone, bisphenol A, and pyrogallol.

Examples of the aldehydes may include formaldehyde, acetoaldehyde, benzaldehyde, and terephthalaldehyde.

Examples of the ketones may include acetone, methyl ethyl ketone, diethyl ketone, and diphenyl ketone.

These condensation reactions can be performed according to an ordinary method.

The vinylphenol polymer is selected from a homopolymer of vinylphenol(hydroxystyrene) and copolymers thereof with copolymerizable component. Examples of the copolymerizable component may include acrylic acid, methacrylic acid, styrene, maleic anhydride, maleimide, vinyl acetate, acrylonitrile, and derivatives thereof.

The isopropenylphenol polymer is selected from a homopolymer of isopropenylphenol and copolymers thereof with a copolymerizable component.

Examples of the copolymerizable component may include acrylic acid, methacrylic acid, styrene, maleic anhydride, maleimide, vinyl acetate, acrylonitrile, and derivatives thereof.

Examples of the low-molecular weight polyphenolic compound may include carixarene derivatives and compounds represented by the following general formulas (31) to (36):

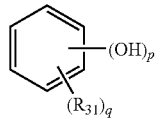
(31)

wherein $R_{31}$ is an alkyl group having 1-4 carbon atoms, phenyl group, or 1-naphthyl group; a plurality of $R_{31}$ may be the same or different from each other; p is an integer of 1 or more; and q is an integer of 0 or more with the proviso that $p+q \leq 6$.

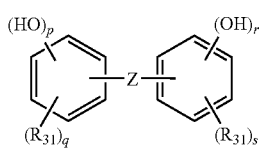
(32)

wherein $R_{31}$ is the same as in the general formula (31): Z is a single bond, —S—, —O—, —CO—, —COO—, —SO—, —C($R_{32}$)$_2$— (where $R_{32}$ is a hydrogen atom an alkyl group having 1-6 carbon atoms, an acryl group having 2-11 carbon atoms, a phenyl group, or a naphthyl group, and a plurality of $R_{32}$ may be the same or different from each other), or a group represented by the following general formula (33):

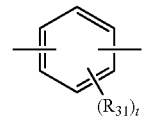
(33)

wherein $R_{31}$ is the same as in the general formula (31), and t is an integer of 0-4; and p, q, r and s are respectively an integer of 0 or more satisfying $p+q \leq 5$, $r+s \leq 5$, and $p+r \geq 1$.

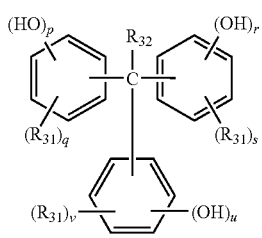
(34)

wherein $R_{31}$ is the same as in the general formula (31); $R_{32}$ is the same as in the general formula (32); and p, q, r, s, u and v are respectively an integer of 0 or more satisfying $p+q \leq 5$, $r+s \leq 5$, $u+v \leq 5$, and $p+r+u \geq 1$.

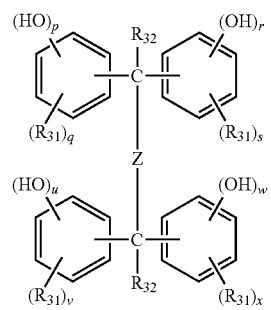
(35)

wherein $R_{31}$ is the same as in the general formula (31); $R_{32}$ and Z are the same as in the general formula (32); a plurality of $R_{31}$ may be the same or different from each other; a plurality of $R_{32}$ may be the same or different from each other; and p, q, r, s, u, v, w and x are respectively an integer of 0 or more satisfying $p+q \leq 5$, $r+s \leq 5$, $u+v \leq 5$, $w+x \leq 5$, and $p+r+u+w \geq 1$.

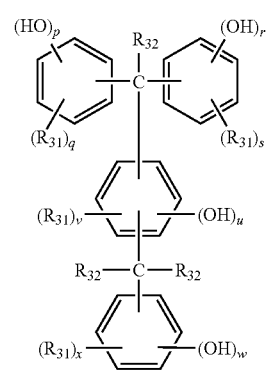
(36)

wherein $R_{31}$ is the same as in the general formula (31); $R_{32}$ is the same as in the general formula (32); a plurality of $R_{31}$ may be the same or different from each other; a plurality of $R_{32}$ may be the same or different from each other; and p, q, r, s, u, v, w and x are respectively an integer of 0 or more satisfying $p+q \leq 5$, $r+s \leq 5$, $u+v \leq 5$, $x+w \leq 4$, and $p+r+u+w \geq 1$.

In the above-described polycondensation reactions, all the phenolic hydroxyl groups are not necessarily required to be coumarinylmethyletherified. It is preferable that, in a molecule, there are two or more coumarinylmethyletherified phenolic groups and a degree of coumarinylmethyletherification is 10% or more and 90% or less, particularly 10% or more and 50% or less.

When the degree of the coumarinylmethyl-etherification is excessively high, resist pattern formation requires a large amount of light exposure and adhesiveness of the resist with respect to a substrate to be processed is low due to a low polarity. When the degree of the coumarinylmethyl-etherification is less than 10%, the resist pattern has low resistance to a developing liquid.

The photosensitive compound of the present invention, e.g., coumarinylmethyl ether directly generates a phenolic hydroxyl group as an alkali-soluble group through a photochemical reaction represented by a reaction formula shown below. In other words, the photosensitive compound functions as a positive resist dissolved in an alkaline developing liquid at an exposed portion.

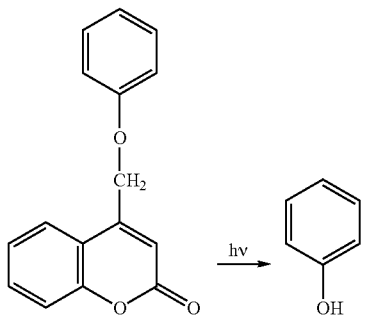

EXAMPLE

During use, the photosensitive compound of the present invention is prepared as a photosensitive composition by being dissolved in a solvent, e.g., with a solid content (concentration) of 0.1 wt. % or more and 50 wt. % or less. The photosensitive composition may desirably be filtered through a filter with a pore diameter of about 0.1-0.2 μm.

The solvent may be basically any solvent and can be selected freely depending on a purpose so long as the solvent dissolves the photosensitive compound of the present invention and cause no reaction with the photosensitive composition.

Examples of the solvent may include: ethers, esters, ether esters, ketones, ketone esters, amides, amide esters, lactams, lactones, and (halogenated) hydrocarbons. More specifically, the solvent may include: ethylene glycol monoalkyl ethers, diethylene glycol dialkyl ethers, ethylene glycol monoalkyl ether acetates, propylene glycol monoalkyl ether acetates, propylene glycol monoalkyl ethers, propylene glycol dialkyl ethers, acetate esters, hydroxyacetate esters, lactate esters, alkoxyacetate esters, cyclic or acyclic ketones, acetoacetate esters, pyruvate esters, propionate esters, N,N-dialkylformamides, N,N-dialkylacetamides, N-alkylpyrrolidones, γ-lactones, (halogenated) aliphatic hydrocarbons, and (halogenated) aromatic hydrocarbons.

Specific examples of the solvents may include: ethylene glycol monomethyl ether, ethylene glycol monoethyl ether, ethylene glycol mono-n-propyl ether, ethylene glycol mono-n-butyl ether, diethylene glycol dimethyl ether, diethylene glycol diethyl ether, diethylene glycol di-n-propyl ether, diethylene glycol di-n-butyl ether, ethylene glycol monomethyl ether acetate, ethylene glycol monoethyl ether acetate, ethylene glycol mono-n-propyl ether acetate, propylene glycol monomethyl ether acetate (PGMEA), propylene glycol monoethyl ether acetate, propylene glycol mono-n-propyl ether acetate, isopropenyl acetate, isopropenyl propionate, toluene, xylene, methyl ethyl ketone, cyclohexanone, 2-heptanone, 3-heptanone, 4-heptanone, ethyl 2-hydroxypropionate, ethyl 2-hydroxy-2-methylpropionate, ethyl ethoxyacetate, ethyl hydroxyacetate, methyl 2-hydroxy-3-methylbutyrate, 3-methoxybutyl acetate, 3-methyl-3-methoxybutyl acetate, 3-methyl-3-methoxybutyl propionate, 3-methyl-3-methoxybutyl butyrate, ethyl acetate, n-propyl acetate, n-butyl acetate, methyl acetoacetate, ethyl acetoacetate, methyl 3-methoxypropionate, ethyl 3-methoxypropionate, methyl 3-ethoxypropionate, ethyl 3-ethoxypropionate, N-methylpyrrolidone, N,N-dimethylformamide, and N,N-dimethylacetamide.

Of these solvents, in consideration of safety, propylene glycol monomethyl ether acetate (PGMEA), ethyl-2-hydroxypropionate, cyclohexanone, and the like may desirably be used. These solvents may be used singly or in mixture of two or more species.

The above-mentioned solvent may contain one or more high-boiling solvents as desired. Examples of the high-boiling solvent may include benzyl ethyl ether, di-n-hexyl ether, diethylene glycol monomethyl ether, diethylene glycol monoethyl ether, acetonylacetone, isophorone, caproic acid, caprylic acid, 1-octanol, 1-nonanol, benzyl alcohol, benzyl acetate, ethyl benzoate, diethyl oxalate, diethyl maleate, γ-butyrolactone, ethylene carbonate, propylene carbonate, and ethylene glycol monophenyl ether acetate.

The photosensitive composition of the present invention may contain a surfactant.

Examples of the surfactant may include: fluorine-containing surfactants; silicone-containing surfactants; polyoxyethylene alkyl ethers such as polyoxyethylene lauryl ether, polyoxyethylene stearyl ether, and polyoxyethylene oleyl ether; polyoxyethylene aryl ethers such as polyoxyethylene octyl phenyl ether, and polyoxyethylene nonyl phenyl ether; and polyoxyethylene dialkyl esters such as polyoxyethylene dilaurate, and polyoxyethylene distearate. By addition of the surfactant, it is possible to control the adhesiveness with respect to the substrate and wettability with respect to the developing liquid.

Commercially available surfactants may include BM-1000, and BM-1100 (BM Chemie Co.); Megafack F142D, F144D, F171, F172, F173, F177, F178A, F178K, F179, F183, F184, and F191 (Dainippon Ink & Chemicals Inc.); Florard FC-135, FC-170C, FC-171, FC-176, FC-430, and FC-431; Megafack RS-1, RS-7, RS-8, RS-9, RS-15, and R-08 (Sumitomo 3M Ltd.); Surflon S-112, S-113, S-131, S-141, S-145, S-382, SC-101, SC-102, SC-103, SC-104, SC-105, and SC-106 (Asahi Glass Co.); F-Top EF301, EF303, and EF 352 (Shin Akita Kasei K. K.); SH-28PA, SH-190, SH-193, SZ-6032, SF-8428, DC-57, and DC-190 (Dow Corning Toray Silicone Co., Ltd.); Organosiloxane Polymer KP341 (Shin-Etsu Chemical Co., Ltd.); (metha)crylate type copolymers Polyflow No. 57, No. 95 (Kyoeisha Kagaku K. K.); Ftargent FT-250, FT-251, and FTX-218 (Neos Co., Ltd.); etc.

These surfactants may be ordinarily used in an amount of 0.2 wt. part or less per the total amount (100 wt. parts) of the photosensitive compound, preferably in an amount of 0.001 wt. part or more and 0.05 wt. part or less, more preferably in an amount of 0.003 wt. part or more and 0.02 wt. part or less.

The photosensitive composition may further contain known additives such as a colorant, an adhesive aid, a storage stabilizer, a defoaming agent, and the like, as desired.

A solution of the photosensitive composition of the present invention can be applied by a known application apparatus such as a spin coater, a dip coater, and a roller coater by a known method. A thickness of the applied film(layer) may be freely set depending on the use of the film but the solution may desirably applied to provide a film(layer) thickness of 0.01 μm or more and 5 μm or less after prebaking.

A material for the substrate onto which the photosensitive composition is applied may include metals, semiconductors, glass, quartz, BN, and organic materials. The substrate may be coated with a single film of or a plurality of films of a resist, a spin-on-glass material, an organic substance, a metal, an oxide, a nitride, or the like.

Examples of the substrate coated with plural kinds of coating films may preferably include a substrate which is coated with an underlying layer of a resist removable by oxygen dry-etching and a layer resistant to oxygen plasma etching formed in this order.

On the oxygen-plasma-etching-resistant layer, the photosensitive resist layer is formed.

Example of the resist for the underlying layer may include thermosetting phenol resin materials, but the resist is not limited thereto.

The oxygen-plasma-etching-resistant layer may be formed from SiO2, TiO2, or a spin-on-glass material, but is not limited thereto.

The underlying layer of the removable resist may preferably be formed in a thickness of 0.01 µm or more and 1 µm or less, and the oxygen-plasma-etching-resistant layer preferably be formed in a thickness of 0.001 µm or more and 1 µm or less.

The applied film of the photosensitive composition may be appropriately prepared depending on the boiling point of the solvent or the like of the photosensitive composition, but may be prebaked at a temperature of 50° C. or more and 150° C. or less, preferably 80° C. or more and 110° C. or less. The prebaking can be performed by a heating means such as a hot-plate, a hot-air drier, or a like.

The thus applied photosensitive composition layer is ordinarily exposed to radiation selectively (e.g., imagewisely) through a mask by using a known exposure device. The radiation for the exposure may include visible rays, ultraviolet rays, far ultraviolet rays, X-rays, electron rays, γ-rays, molecular beams, and ion beams. These rays may be selected and used appropriately. In a preferred embodiment, mercury lamp beams (wavelengths: 436 nm, 365 nm, 254 nm), a KrF excimer laser beam (wavelength: 248 nm), an ArF excimer laser beam (wavelength: 193 nm), a $F_2$ excimer laser beam (wavelength: 157 nm), far ultraviolet beams such as an extreme ultraviolet beam (EUV, wavelength: 13 nm), and electron beams are used. These rays may be employed singly or in mixture of two or more species.

As another exposure method, it is possible to preferably employ a method in which near-field light generated by a photomask including a light-blocking layer having an opening width smaller than the wavelength of exposure light source. As the radiation for the near-field light exposure, the above-mentioned radiation rays can be used. The radiation rays may be used singly or in combination of two or more species. The near-field light exposure is conducted by bringing the light-blocking layer close to (e.g. into close contact with) an object to be exposed.

In order to obtain a finer resist pattern, it is particularly preferable that the exposure is performed with shorter wavelength beams such as ArF excimer laser beams, $F_2$ excimer laser beams, EUV beams, electron beams, and near-field light which is not affected by diffraction limit.

The photosensitive compound of the present invention is capable of causing a photochemical reaction through two-photon excitation. There are two exposure method for effecting the two-photon excitation.

In one method, light of a wavelength which is longer than an absorption edge wavelength, in an ultraviolet-visible region, of the photosensitive compound of the present invention and is not longer than two times the absorption edge waveform is converged (condensed) by a lens to effect light exposure.

By the convergence of the light, the exposure light is converged to a degree of diffraction limit but a region in which an actual two-photon excitation reaction is caused to occur is a further minute region. That is, it is possible to form a resist pattern with a width which is not more than the diffraction limit.

In the other method for effecting the two-photon excitation, a photomask is brought close to (e.g., into close contact with) the layer of the photosensitive compound of the present invention and irradiation with light having a wavelength which is longer than an absorption edge wavelength, in an ultraviolet-visible region, of the photosensitive compound of the present invention and is not longer than two times the absorption edge wavelength. In the neighborhood of an edge of a photomask light-blocking material, a particularly strong electric field as the near-field light is generated, so that the two-photon excitation occurs only in the neighborhood of the edge. That is, it is possible to form a resist pattern with a minute pitch smaller than a pattern pitch of the photomask. The photosensitive compound of the present invention has an absorption edge of about 500 nm, so that a light source with a wavelength of 550-1000 nm may desirably be used as a light source used for the two-photon excitation. As such a light source, it is possible to use a YAG laser, titanium-sapphire laser, a carbon dioxide laser, a helium-neon laser, and a semiconductor laser. The titanium-sapphire layer is particularly desirable.

Next, the photochemical reaction of the photosensitive composition of the present invention will be described.

Figure 2:
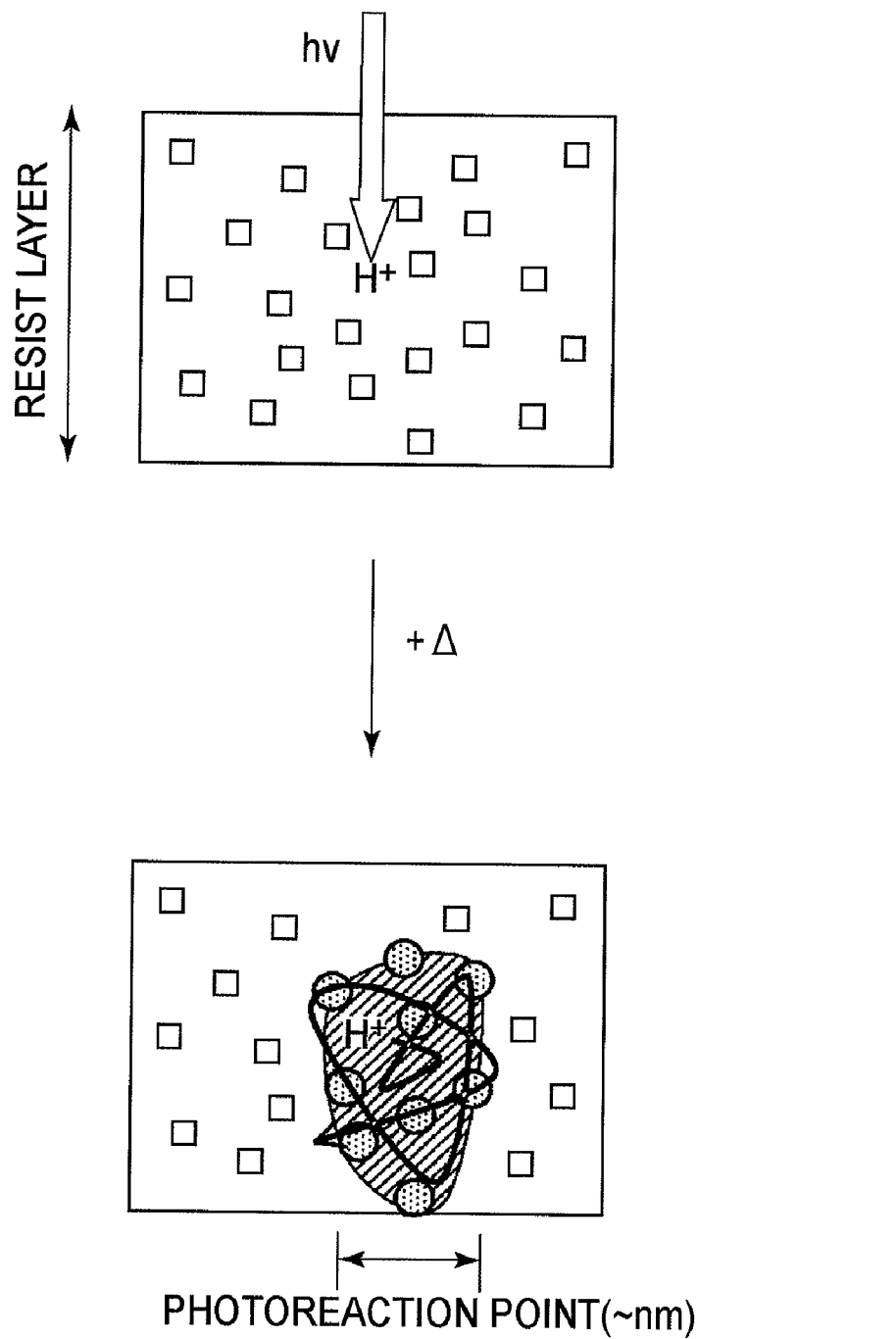
FIG. 2 is a schematic view for illustrating a photochemical reaction of a conventional chemically amplified resist.

FIG. 1 is a schematic view for illustrating a photochemical reaction of the photosensitive composition of the present invention and FIG. 2 is a schematic view for illustrating a photochemical reaction of a conventional chemically amplified resist.

In the resist shown in FIG. 2, one photon generates one acid functioning as a catalyst and the acid induces a plurality of deprotection reactions while diffusing by heating before development to produce a plurality of alkali-soluble groups. On the other hand, in the present invention, the heating before the development performed in the conventional chemically amplified resist is not required. Here, a photoreaction point (spot) referred to in the present invention is defined as a region in which one photon is capable of induce the deprotection reaction as shown in FIG. 1.

In the chemically amplified resist, one photon generates one acid functioning as a catalyst and the acid induces a plurality of deprotection reactions while diffusing by heat, whereas in the photosensitive compound of the present invention, one photon induces one deprotection reaction.

Therefore, one photoreaction point in the chemically amplified resist has a size of about 10 nm. On the other hand, the photoreaction point of the photosensitive compound of the present invention has a size of a molecular scale (0.1 nm or more and 1 nm or less), so that a resist pattern can be formed with a small LER.

After the exposure, the irradiated portion (exposed portion) of the photosensitive composition is developed and removed to obtain an intended resist pattern.

Examples of the alkaline developing liquid used for the development may include aqueous alkaline solutions containing compounds dissolved therein, such as sodium hydroxide, potassium hydroxide, sodium carbonate, sodium silicate, sodium metasilicate, ammonia, ethylamine, n-propylamine, diethylamine, di-n-propylamine, triethylamine, methyldiethylamine, dimethylethanolamine, triethanolamine, tetramethylammonium hydroxide, tetraethylammonium hydroxide, pyrrole, piperidine, choline, 1,8-diazabicyclo[5.4.0]-7-undecene, and 1,5-diazabicyclo[4.3.0]-5-nonene. To these aqueous alkaline solutions, it is also possible to add a water-soluble organic solvent such as methanol, and ethanol, or a surfactant in an appropriate amount. An aqueous 2.38 wt. %-tetramethylammonium hydroxide solution is particularly preferred.

The development may be conducted by dipping, spraying, brushing, slapping, or a like method. Thereafter, the resist is washed and dried to obtain a desired resist pattern.

In the case where the resist pattern is formed in a film on a substrate having an underlying layer of a resist removable by oxygen dry-etching and an oxygen-plasma-etching-resistant layer formed thereon in this order, firstly the oxygen plasma-etching-resistant layer is etched through the above-mentioned resist pattern as the mask. For the etching, wet etching and dry etching are applicable but the dry etching is suitable for fine pattern formation and is preferred. An etchant for the wet etching is selected depending on an object to be etched, and examples thereof may include hydrofluoric acid solutions, aqueous ammonium fluoride solutions, aqueous phosphoric acid solutions, aqueous acetic acid solutions, aqueous nitric acid solutions, and aqueous cerium ammonium nitrate solutions.

The gas for the dry etching may include $CHF_3$, $CF_4$, $C_2F_6$, $SF_6$, $CCl_4$, $BCl_3$, $Cl_2$, HCl, $H_2$, and Ar, and the like gas. These gases may be used in mixture, as desired.

Next, oxygen plasma etching is conducted through the pattern of the oxygen-plasma-etching-resistant layer, as the mask, onto which the resist pattern is transferred. The oxygen-containing gas used for the oxygen plasma etching may include, e.g., oxygen alone, mixtures of oxygen with an inert gas such as argon, mixtures of oxygen with carbon monoxide, carbon dioxide, ammonia, dinitrogen monoxide, or sulfur dioxide.

Through the above two-step etching, a resist pattern can be formed with a higher aspect ratio than a resist pattern after the exposure and the development.

With the resist pattern formed as described above as the mask, a substrate is processed by dry etching, wet etching, metal vapor deposition, lift-off, plating, and the like. As a result, it is possible to produce a desired device. More specifically, a semiconductor device can be prepared in the following manner.

Firstly, a device circuit of a semiconductor is designed, and a mask on which a circuit pattern is formed based on the design is prepared. Separately, a substrate for the device (e.g., a silicon wafer) is prepared, and thereon the photosensitive composition of the present invention is laminated.

Then, the circuit is formed on the substrate through lithography by using the mask and an ordinarily used exposure device or the like. For formation of the circuit, steps of oxide film formation, etching, insulation film formation, conductive wiring film formation, and patterning are performed. Next, the substrate on which the circuit is formed is subjected to an assembly process (dicing, and bonding), packaging, and the like, and then is chipped.

The present invention can be utilized for a resist pattern forming method using a photosensitive composition capable of forming a resist pattern with a low LER and a substrate processing method using the resist pattern.

Next, a specific synthesis example of the photosensitive compound will be described.

Synthesis Example of Photosensitive Compound of Formula (5)

In a 50 ml-reaction vessel, polyhydroxystyrene(1.0 g, 8.32 mmol, 1.0 eq) and N,N-dimetylformamide(10 ml) were placed and heated to 50° C. in nitrogen atmosphere. To this solution, NaH (40 mg, 1.67 mmol, 0.20 eq) was added and stirred for 1 hour and 4-bromomethyl-6,7-dimethoxycoumarin (0.42 g, 1.39 mmol, 0.167 eq) was added at a time, followed by stirring for 1 hour at 50° C. To this solution, NaH (40 mg, 1.67 mmol, 0.20 eq) was added again and stirred for 1 hour and to the resultant suspension, 4-bromomethyl-6,7-dimethoxycoumarin (0.42 g, 1.39 mmol, 0.167 eq) was added at a time, followed by stirring for 1 hour at 50° C. Then, to the suspension, NaH (40 mg, 1.67 mmol, 0.20 eq) was added again and stirred for 1 hour and to the resultant suspension, 4-bromomethyl-6,7-dimethoxycoumarin (0.41 g, 1.35 mmol, 0.162 eq) was added at a time, followed by stirring for 1 hour at 50° C. Thereafter, heating of the resultant solution was stopped and the solution was stirred for 18 hours as it was. The resultant solution was added into a mixture of 10%-aqueous ammonium hydrochloride solution(30 ml) and distilled water(120 ml), followed by extraction with ethyl acetate (20 ml×3). The resultant organic layers were evaporated together concentrated. The resultant concentrate was dispersed in diethyl ether and filtered to precipitate a crystal. The crystal was sufficiently washed with diethyl ether and dried at 50° C. in high vacuum to obtain yellow powder(1.84 g). To this powder, toluene(40 ml) was added, followed by vigorous stirring for 2 hours at room temperature. Thereafter, the powder was recovered by filtration. The resultant powder was washed with toluene(10 ml) and dried at 50° C. in high vacuum to obtain a photosensitive compound having the structural unit represented by the general formula(5) (1.46 g, introduction degree:35.6% to 44.4%).

While the invention has been described with reference to the structures disclosed herein, it is not confined to the details set forth and this application is intended to cover such modifications or changes as may come within the purpose of the improvements or the scope of the following claims.

This application claims priority from Japanese Patent Application No. 027367/2007 filed Feb. 6, 2007, which is hereby incorporated by reference.

What is claimed is:

1. A photosensitive compound comprising:
two or more structural units, in a molecule, represented by the following general formula (2):

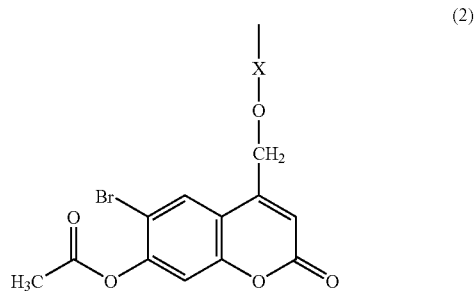

(2)

wherein X is a substituted or unsubstituted phenylene group or a substituted or unsubstituted naphthylene group.

2. A photosensitive compound comprising:
two or more structural units, in a molecule, represented by the following general formula (3):

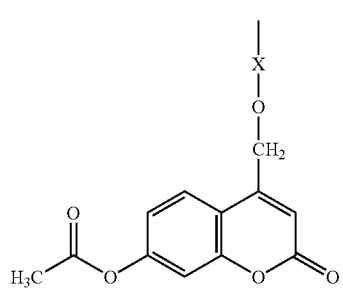

wherein X is a substituted or unsubstituted phenylene group or a substituted or unsubstituted naphthylene group.

3. A photosensitive compound comprising:
two or more structural units, in a molecule, represented by the following general formula (6):

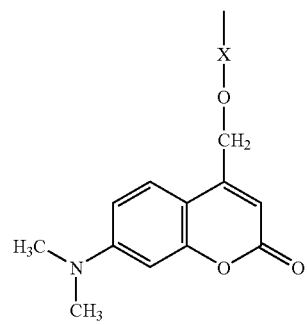

wherein X is a substituted or unsubstituted phenylene group or a substituted or unsubstituted naphthylene group.

4. Polyhydroxystyrene comprising:
hydrogen atoms of two or more phenolic hydroxyl groups substituted with a substituent represented by the following general formula (7):

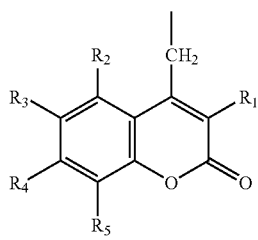

wherein $R_1$ to $R_5$ are selected from the group consisting of hydrogen atom, halogen atom, alkyl group, alkoxy group, acetoxy group, phenyl group, naphthyl group, and alkyl group in which a part or all of hydrogen atoms are substituted with fluorine atom.

5. Novolak resin comprising:
hydrogen atoms of two or more phenolic hydroxyl groups substituted with a substituent represented by the following general formula (7):

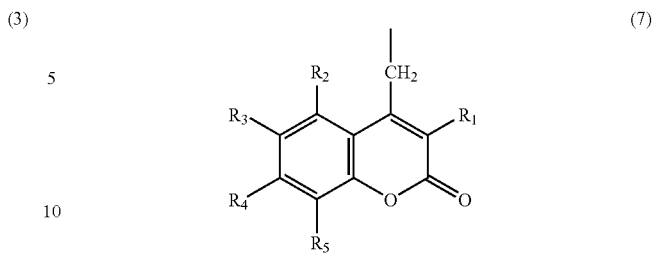

wherein $R_1$ to $R_5$ are selected from the group consisting of hydrogen atom, halogen atom, alkyl group, alkoxy group, acetoxy group, phenyl group, naphthyl group, and alkyl group in which a part or all of hydrogen atoms are substituted with fluorine atom.

6. A resist pattern forming method comprising:
a step of forming a photosensitive resist layer by applying a photosensitive composition onto a substrate;
a step of selectively irradiating the resist layer with radiation; and
a step of forming a pattern of the resist layer by developing an irradiated portion of the resist layer,
wherein the photosensitive composition comprises at least one species of a photosensitive compound and an organic solvent in which said at least one species of the photosensitive compound is dissolved, and
wherein the photosensitive compound comprises two or more structural units, in a molecule, represented by the following general formula (1):

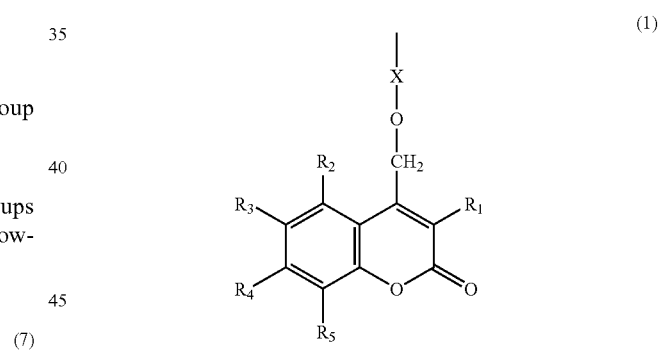

wherein $R_1$ to $R_5$ are selected from the group consisting of hydrogen atom, halogen atom, alkyl group, alkoxy group, acetoxy group, phenyl group, naphthyl group, and alkyl group in which a part or all of hydrogen atoms are substituted with fluorine atom; and X is a substituted or unsubstituted phenylene group or a substituted or unsubstituted naphthylene group.

7. A method according to claim 6, wherein a resist layer removable by plasma etching and a resist layer resistant to oxygen plasma etching are formed on the substrate and thereafter on the resist layer resistant to the oxygen plasma etching, the photosensitive resist layer is formed.

8. A method according to claim 6, wherein the photosensitive resist layer is formed in a thickness of 20 nm or less.

9. A method according to claim 6, wherein the radiation comprises near-field light.

10. A method according to claim 6, wherein the resist layer is irradiated with light, converged by a lens, having a wavelength which is longer than an absorption edge wavelength of the photosensitive compound and is not longer than two times the absorption edge wavelength.

11. A method according to claim 6, wherein a photomask is brought close to the resist layer and the resist layer is irradiated with light having a wavelength which is longer than an absorption edge wavelength of the photosensitive compound and is not longer than two times the absorption edge wavelength.

12. A process for producing a device, comprising:
producing a device on a substrate by using a resist pattern forming method according to claim 6.

13. A process according to claim 12, wherein the substrate on which the pattern of the resist layer is formed is subjected to at least one of dry etching, wet etching, metal vapor deposition, lift-off, and plating.

* * * * *